United States Patent
Kern

(10) Patent No.: US 10,543,062 B2
(45) Date of Patent: Jan. 28, 2020

(54) TOP PIECE FOR A CORRESPONDING PIN-SHAPED DENTAL IMPLANT

(71) Applicant: Mario Kern, Kramsach (AT)

(72) Inventor: Mario Kern, Kramsach (AT)

(*) Notice: Subject to any disclaimer, the term of this patent is extended or adjusted under 35 U.S.C. 154(b) by 308 days.

(21) Appl. No.: 14/482,393

(22) Filed: Sep. 10, 2014

(65) Prior Publication Data
US 2015/0017604 A1    Jan. 15, 2015

Related U.S. Application Data

(63) Continuation of application No. PCT/AT2013/000045, filed on Mar. 12, 2013.

(30) Foreign Application Priority Data

Mar. 14, 2012  (AT) .................................. A 310/2012

(51) Int. Cl.
*A61C 8/00* (2006.01)
*A61C 13/00* (2006.01)

(52) U.S. Cl.
CPC ............ *A61C 8/005* (2013.01); *A61C 8/0068* (2013.01); *A61C 8/0078* (2013.01);
(Continued)

(58) Field of Classification Search
CPC ........ A61C 8/0048; A61C 8/005–0074; A61C 13/0003; A61C 13/0004; A61C 13/0005;
(Continued)

(56) References Cited

U.S. PATENT DOCUMENTS 4,850,873 A   7/1989  Lazzara et al.
6,315,563 B1  11/2001 Sager
(Continued)

FOREIGN PATENT DOCUMENTS

DE   2 139 683   2/1973
EP   1 069 868   1/2001
(Continued)

OTHER PUBLICATIONS

International Search Report (ISR) dated Jul. 24, 2013 in International (PCT) Application No. PCT/AT2013/000045.
(Continued)

*Primary Examiner* — Garrett K Atkinson
(74) *Attorney, Agent, or Firm* — Wenderoth, Lind & Ponack, L.L.P.

(57) ABSTRACT

A top piece for a corresponding pin-shaped dental implant with a platform, which features a first platform surface and a second platform surface, a retention pin placed onto the first platform surface, for mounting of a mesostructure, a connecting pin for connecting the platform with a blind bore of a pin-shaped dental implant corresponding to the connecting pin, while in a first version, an edge of the platform is bulged in a direction oriented away from the connection pin, and in a second version, a diameter of the platform is large enough, at least in a part of a total angular area that, where the top piece is connected to the corresponding pin-shaped dental implant, in a view from above onto the second platform surface, the platform protrudes over the corresponding pin-shaped dental implant.

67 Claims, 4 Drawing Sheets

(52) U.S. Cl.
CPC ...... *A61C 13/0007* (2013.01); *A61C 13/0022* (2013.01); *Y10T 29/49567* (2015.01)

(58) Field of Classification Search
CPC .......... A61C 13/0006; A61C 13/00224; A61V 13/0007
USPC ......... 433/72–76, 172–176, 201.1, 218–223, 433/225
See application file for complete search history.

(56) References Cited

U.S. PATENT DOCUMENTS

| | | | | |
|---|---|---|---|---|
| 7,264,469 | B2* | 9/2007 | Abarno | A61C 1/084 433/173 |
| 8,740,615 | B2* | 6/2014 | Ishiwata | A61C 8/0066 433/173 |
| 2002/0004189 | A1* | 1/2002 | Hurson | A61C 8/005 433/173 |
| 2003/0031981 | A1 | 2/2003 | Holt | |
| 2005/0100863 | A1* | 5/2005 | Chang | A61C 8/0018 433/173 |
| 2005/0153261 | A1* | 7/2005 | Chang | A61C 8/0018 433/173 |
| 2006/0084035 | A1* | 4/2006 | Volz | A61C 8/0012 433/173 |
| 2008/0014556 | A1 | 1/2008 | Neumeyer | |
| 2010/0159419 | A1* | 6/2010 | Grant | A61C 8/001 433/174 |
| 2010/0304334 | A1* | 12/2010 | Layton | A61C 8/005 433/173 |
| 2012/0301850 | A1 | 11/2012 | Sollberger et al. | |

FOREIGN PATENT DOCUMENTS

| | | |
|---|---|---|
| GB | 2484992 | 5/2012 |
| WO | 01/49199 | 7/2001 |
| WO | 2011/089057 | 7/2001 |

OTHER PUBLICATIONS

Austrian Patent Office Search (ASR) Report dated Jul. 18, 2012 in Austrian Patent Application No. A 310/2012.

* cited by examiner

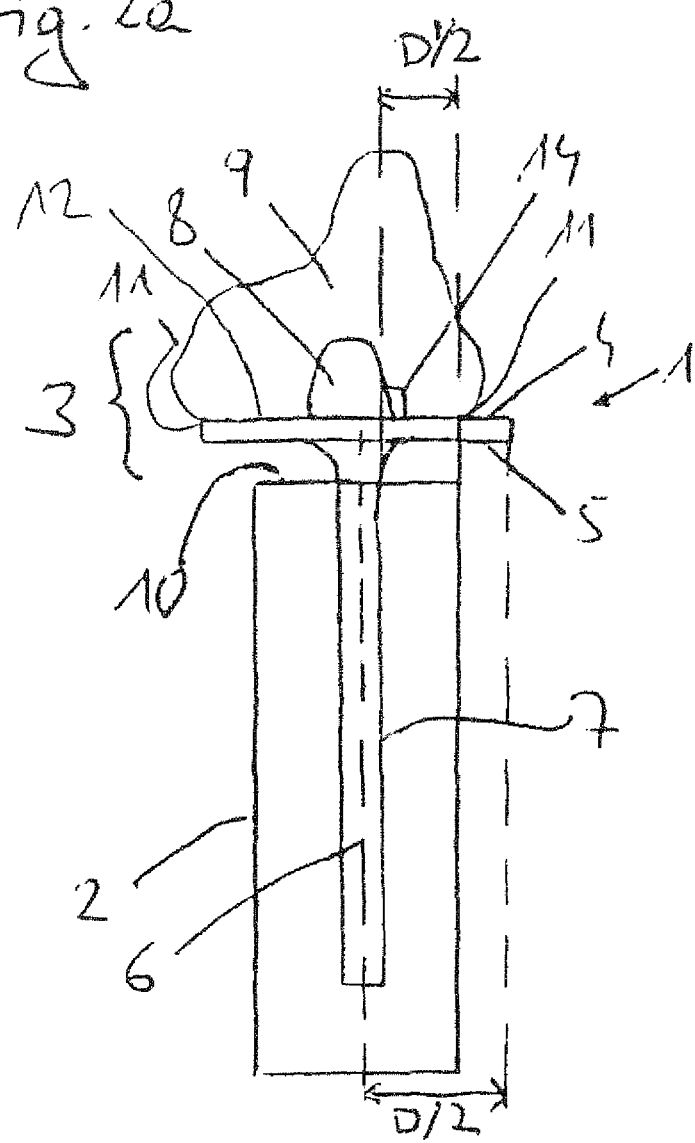
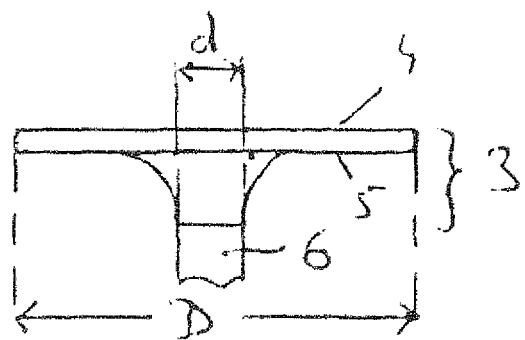

TOP PIECE FOR A CORRESPONDING PIN-SHAPED DENTAL IMPLANT

BACKGROUND OF THE INVENTION

The present invention refers to a top piece for a corresponding pin-shaped dental implant, a positioning with a pin-shaped dental implant and such a top piece, as well as a procedure for the anatomic adaptation of such a top piece.

Specific top parts are used for mounting of a mesostructure, usually made out of ceramic material, onto a dental implant disposed in the jawbone of a patient. The arrangement of the top piece and mesostructure is indicated in the abutment.

For each top piece, there is a corresponding pin-shaped dental implant, whereby a certain top piece is only suitable for the corresponding pin-shaped dental implant, due to the dimensions of the connecting pin and the corresponding blind bore of the pin-shaped dental implant. This is usually indicated by marking or coding (e.g., an inscription or color coding) applied to the corresponding top piece or by an obvious arrangement of the packaging of the top piece. There are indeed also some pin-shaped dental implants, with different outer diameters, which can have a blind bore with the same dimensions, so that a top piece can be used for all pin-shaped dental implants with this type of blind bore. In this case, however, the pin-shaped dental implants with the same blind bore create an equivalence class and the top piece can only be used in view of this equivalence class.

In case the top piece is connected with a pin-shaped dental implant, the platform is defined as that part of the top piece, which connects to the connecting pin of the top piece and protrudes (vertically) over the implant shoulder.

Well-known top pieces have a platform, which is flat, that means not curved. It is also known as a top piece with platform.

See, for example, US 2003/0031981 A1, in which the edge is arched towards the connecting pin.

In the state of the art, the outer diameter of the platform is usually sufficiently larger than the diameter of the connecting pin on an end towards the second surface of the platform (pin diameter), so that it corresponds to the thickness of the blind bore of the dental implant in the area of the implant shoulder, so that the platform is flush mounted with the top piece connected to the dental implant (the diameter of the pin-shaped dental implant must be measured, of course, at the implant shoulder of the pin-shaped dental implant).

Genre specific top pieces result, for example, from WO 2011/089057 A1 and EP 1 069 868 B1 (both: Camlog Technologies AG).

Genre specific top pieces differentiate themselves from so-called gingiva formers through the inclusion of a retention pin for the mounting of the mesostructure. Gingiva formers are not used, however, for the mounting of a mesostructure, but only for the temporary forming of the gingiva.

After the implantation of a dental implant in the jawbone of the patient and the fixation of the abutment on the dental implant, the growth of cells on the dental implant and the abutment, is of higher importance. Studies showed that there is sufficient cell development in the area of the dental implant. In the area of the abutment, the accumulation of cells is usually not that satisfactory.

After the implantation of a dental implant, there is also the possibility of bacterial infestation, especially in the area of the adhesive joint—which is the area, where the mesostructure adjoins the platform—and which could spread into areas of the dental implant.

Genre specific platforms are structured without taking into account the dimensions of the patient's teeth, which adjoin the mesostructure to be mounted on the platform, which exacerbate the above-noted disadvantages.

SUMMARY OF THE INVENTION

The purpose of the invention is the provision of a top piece, of an arrangement made out of a pin-shaped dental implant and a top piece, as well as a procedure for the forming of a platform, which improves the growth of cells and reduces the danger of a bacterial infestation of the dental implant.

The advantageous forms of execution of the invention are defined in the corresponding claims.

The protection of the adhesive joint of the dental implant can take place in one variant of the invention, by forming the edge of the platform in a coronal direction, away from the connecting pin.

In the case of a different variant of the invention, the provision is made, that in the case of a platform connected to the corresponding pin-shaped dental implant, the platform (with a top view on the second platform surface) will protrude over the corresponding pin-shaped dental implant, thus, after the mounting of the mesostructure on the platform, moving the adhesive joint away from the dental implant, as compared to the current state of the art. There can also be protection of the adhesive joint from the dental implant, by means of the platform. This reduces the danger of a bacterial infestation of the dental implant. Additionally, the invention offers a second, increased, platform surface for the growth of cells (epithelial cells and connective tissue cells).

Both variants of the invention can also be used in combination.

If one would look at a top piece according to the invention, in isolation, one would notice that, in the view from above onto the second surface of the platform, the diameter of the platform is significantly larger than the diameter of the pin, at least over the part of the total angular range.

In the case of the variant of the invention, the platform protrudes thus, at least over a part of the total angular range, radially over the corresponding pin-shaped dental implant. In other words, the diameter of the platform above this part of the total angular range is greater than the diameter of the corresponding pin-shaped dental implant in the area of the implant shoulder. Preferably, the diameter of the platform will be 1 to 4 millimeters larger than the diameter of the corresponding pin-shaped dental implant on the implant shoulder.

As a result of the larger diameter of the platform (as compared to the current state of technology), there is also the additional possibility of adapting the platform to the sizes of the mesostructure to be mounted onto the platform, adapted to the neighboring teeth of a patient, by removing the excess material over the parts of the total angular range from the body of the patient—by milling them off, for example.

As with the current state of technology, the top piece according to the invention is formed for a corresponding pin-shaped dental implant (or an equivalence class thereof). This can be indicated, as is known, by a corresponding marking or coding (e.g., an inscription or color coding) on the top piece or an obvious arrangement of the packaging of the top piece.

The top piece can be made of metallic (titanium is especially preferred) or ceramic materials.

The platform structure around the retention pin is preferably formed as a setting shoulder for the mesostructure. As is known, the top piece can have an axially arranged bore hole, which extends through the connection pin and which allows the screwing of the top piece on the dental implant.

The second surface of the platform can either continue in the direction of the connecting pin, it can taper off towards the diameter of the pin, or the transition can take place in the form of a step.

A configuration of the top piece with a pin-shaped dental implant, which supports platform switching, is to be preferred. The top piece and the dental implant are formed especially for an individual tooth implant, or as an individual tooth implant.

It is possible, that a processing sleeve is placed as protection for the connecting pin, during processing of the platform. After completing the processing—e.g., sandblasting the platform—the processing sleeve may be removed from the connecting pin.

BRIEF DESCRIPTION OF THE DRAWINGS

FIGS. 2a and 2b illustrate an embodiment of the dental implant according to the invention;

DETAILED DESCRIPTION OF THE INVENTION

Figure 1:
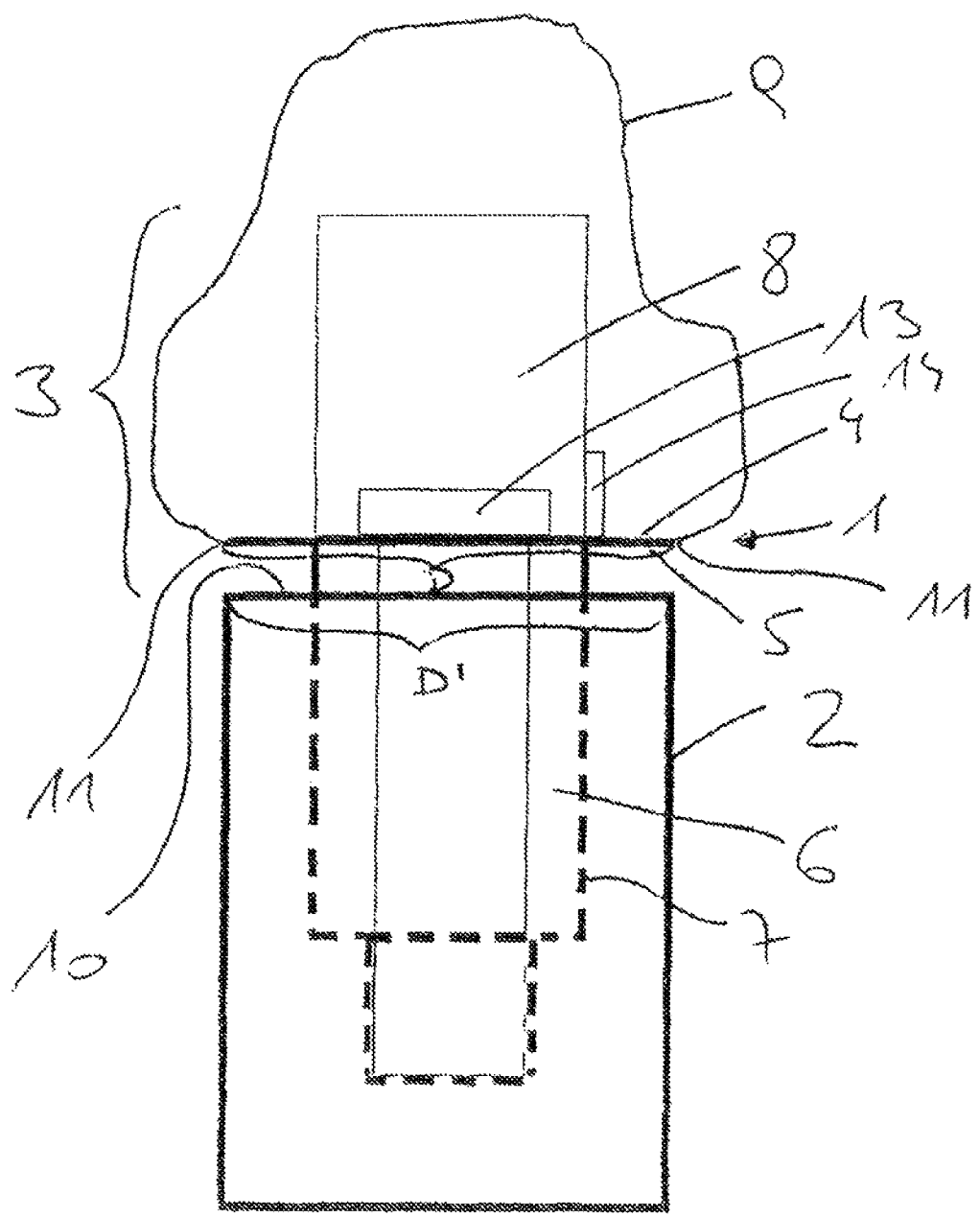
FIG. 1 shows a top piece, according to the current state of technology as indicated in FIG. 1.

FIG. 1 displays an example of a top piece 1 (with platform switching) according to the state of the technology, in a section displaying the middle longitudinal axis of the arrangement.

The top piece 1 features a platform 3 with a first platform surface 4 and a platform surface 5. The platform 3 features a diameter D. On the first surface of the platform 4, there is a retention pin 8 (with an anti-rotation lock 14) for the mounting of the mesostructure 9. A connecting pin 6 is located on the second platform surface 5.

The corresponding pin-shaped dental implant 2 features a blind bore 7, whose dimensioning is adapted to the connecting pin 6. The platform 3 is formed with a smaller diameter in the area of the implant shoulder 10, as a pin-shaped dental implant 2 (platform switching). In the view from above, the second surface of the platform 5 is flush with the pin-shaped dental implant, and its diameter D is thus selected at the same size as the diameter D' of the pin-shaped dental implant 2. The distance between the adhesive joint 11 and the pin-shaped dental implant 2 is very small, which can lead to a bacterial infestation of the pin-shaped dental implant 2. Additionally, the second platform surface 4 only features a small surface for the desired accumulation of cells.

FIGS. 2a and 2b show a first execution example of the invention, in a section oriented on the middle of the longitudinal axis of the arrangement.

The top piece 1 features a platform 3 with a first platform surface 4 and a second platform surface 5. The platform 3 is formed with a circular circumference in the area of the first and second platform surfaces 4, 5 and features a diameter D. The first platform surface 4 features a retention pin 8 for the mounting of the mesostructure 9. The second platform surface 5 features a connecting pin 6. The first platform surface is formed around the retention pin 8 as a setting shoulder 12 (circular, around the retention pin 8) for the mesostructure 9. As is well known, the top piece 1 can feature an axially arranged borehole, which extends to the connecting pin 6 and which allows the screwing of the top piece 1 onto the pin-shaped dental implant 2, by means of a screw 13. The connecting pin 6 and the blind bore 7 can feature, at least for certain parts of their lengths, the corresponding threads.

The corresponding pin-shaped dental implant 2 features a blind bore 7, whose dimensioning is adapted to the connecting pin 6. In the area of the implant shoulder 10, the platform 3 is formed with a smaller diameter as the pin-shaped dental implant 2 (platform switching). In a view from above on the second platform surface 5, platform 3 features a larger diameter D, than the pin-shaped dental implant 2 in the area of the implant shoulder 10 (diameter D'), thus platform 3 protrudes over the corresponding pin-shaped dental implant 2. The adhesive joint 11 is protected by platform 3 from the pin-shaped dental implant 2. A bacterial infestation of the pin-shaped dental implant 2 is thus made more difficult, if not avoided altogether. The second platform surface 5 features a larger surface for the desired settlement of cells.

FIG. 2b indicates in a detailed view the platform 3 and the second platform surface 5 near the end of the connecting pin 6 (the retention pin 8 is not displayed). The ratio between the diameter D and the pin diameter d is shown.

Figure 3:
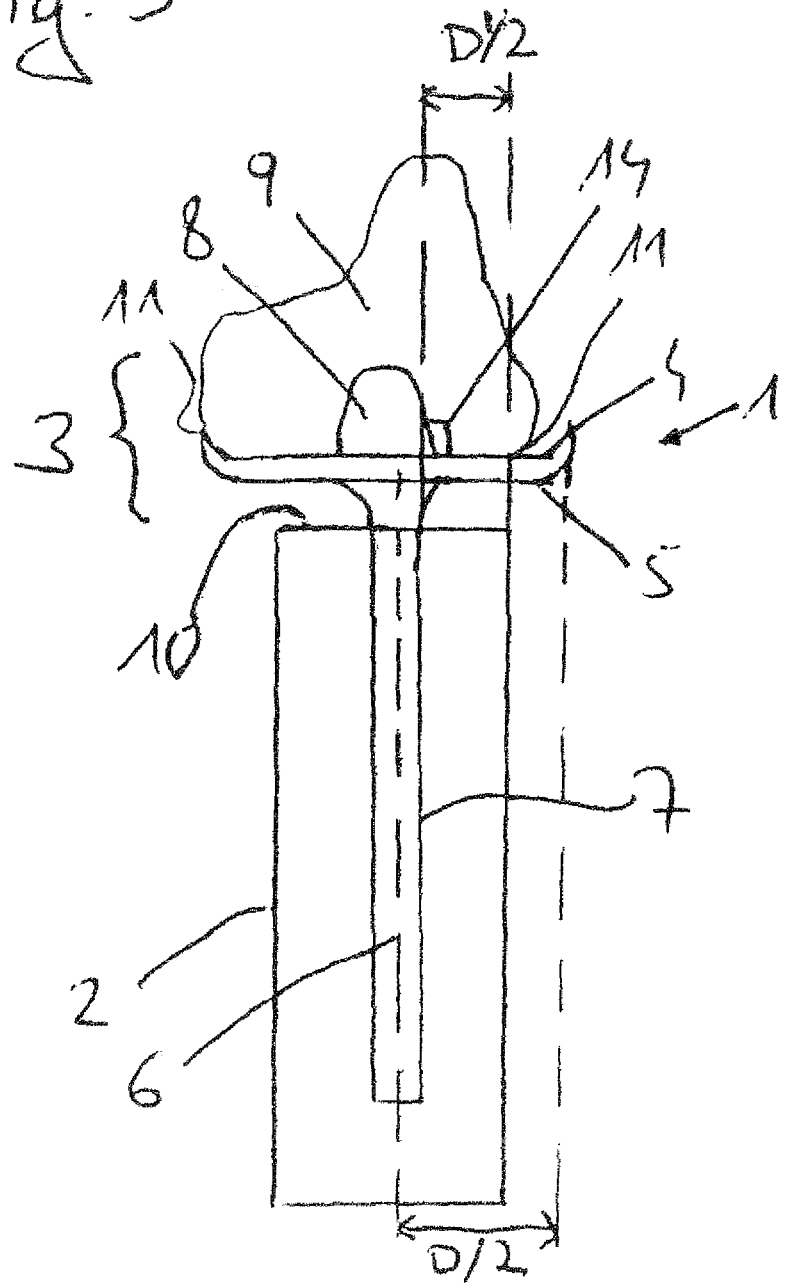
FIG. 3 shows a second embodiment of the dental implant according to the invention.

FIG. 3 indicates a second execution example of the invention, in a section indicating the middle longitudinal axis.

The execution example of FIG. 3 is different from the one in FIG. 2 only by the fact that the edge of the platform 3 is arched in a coronal direction, away from the connecting pin 6, which results in a plate-like formation of the first platform surface 4 (over the entire angular range φ1, φ2, φ3, φ4). Additionally, the platform 3 is tapered in the direction of its edge (the thickness of the platform 3, generated by the distance between the first and second platform surfaces 4, 5 is smaller than in the center of the platform 3). The thickness of the platform 3, before the area where it starts tapering, can be, for example, 0.8 millimeters.

These two measures (bulging and tapering) can also be applied individually, which means independently from each other. The bulging can also take place independently from the diameter of the platform.

Otherwise, the top piece 1 is formed exactly as in the representation in FIG. 2. For reasons of clarity, not all the details represented in FIG. 2 are represented again in FIG. 3.

Unlike the representation in FIGS. 2 and 3, there is also the possibility of using top pieces 1 without platform switching, according to the invention. In this case, the second platform 5 would connect directly (without the tapered part in the direction of the connecting pin 6) to the connecting pin 6 and be supported by the implant shoulder 10 or at least indicate only a minimal distance to it.

Figure 4A:
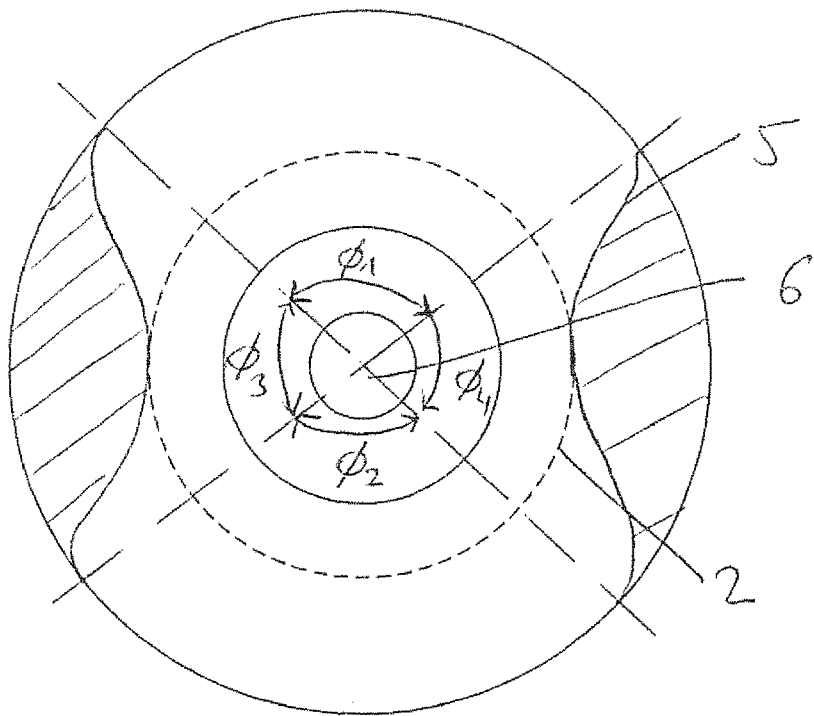
FIGS. 4a and 4b are plan views of the dental implants shown in FIGS. 1 and 3, respectively.
Figure 4B:
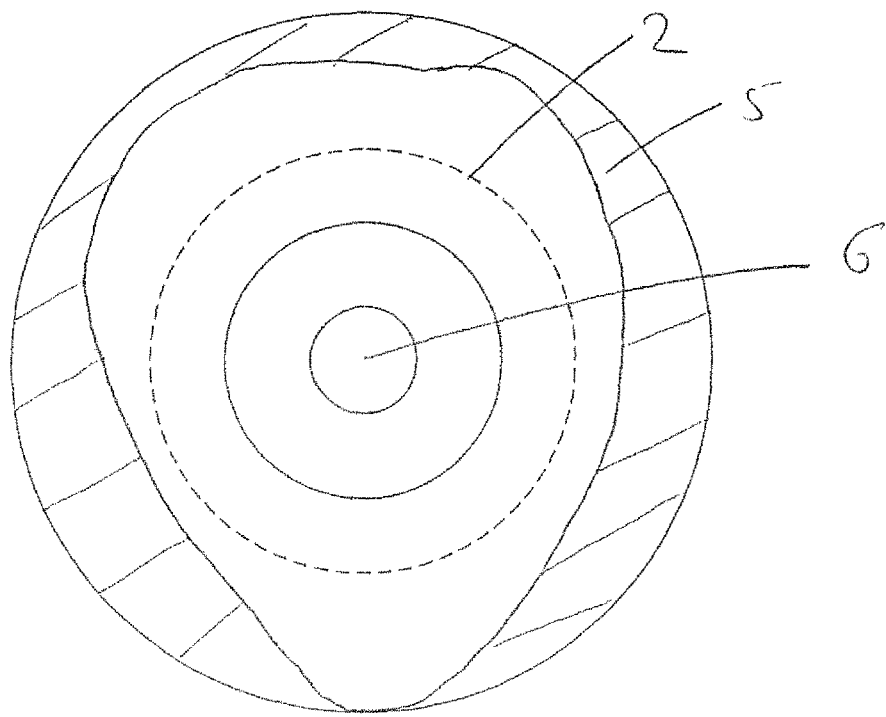

FIGS. 4a and 4b indicate a top piece 1 according to FIG. 1 or FIG. 3 in a view from above onto the second level of the platform 5, while different anatomical adaptations were performed on the platform 3, bearing in mind the dimensions of the patient's teeth, adjoining the mesostructure to be mounted onto the platform 3.

The corresponding hatched areas of the platform 3 are removed by removing the material. Before removing the material, the platforms 3 are formed in a view from above onto the first or second platform surface 4, 5, preferably with a circular circumference.

Thus, there are platforms 3, for which the diameter D of the platform 3 is only large enough over a part of $\phi1$, $\phi2$ of the total angular area $\phi1$, $\phi2$, $\phi3$, $\phi4$ ($\phi1+\phi2+\phi3+\phi4=360°$), that a top piece 1, connected with a corresponding pin-shaped dental implant 2, and the platform 3 will protrude in a view from above onto the platform surface 5 over the corresponding pin-shaped dental implant 2. In the areas $\phi3$, $\phi4$ of the total angular area $\phi1$, $\phi2$, $\phi3$, $\phi4$, the platform 3 is flush, in a view from above onto the second platform surface 5, with the pin-shaped dental implant 2.

In contrast to the representation, the retention pin 8 must not necessarily create a right angle with the first platform surface 4.

The material removal could also be selected in such a way, that the diameter D of the platform 3, remains large enough over the total angular area $\phi1$, $\phi2$, $\phi3$, $\phi4$, that the top piece 1, connected to the corresponding pin-shaped dental implant 2, will protrude in a view from above onto the second platform surface 5, over the corresponding pin-shaped dental implant 2, but at a different width, according to the angular area.

The invention claimed is:

1. A top piece for a corresponding pin-shaped dental implant, the top piece comprising:
    a platform having a first platform surface and a second platform surface,
    a retention pin mounted on the first platform surface for fastening of a mesostructure, and
    a connecting pin for connecting the platform with a blind bore of a pin-shaped dental implant corresponding to the connecting pin,
    wherein:
        an edge of the platform is arched in a coronal direction, away from the connecting pin, which results in a plate-shaped formation of the first platform surface such that a central portion of the first platform surface is flat, and
        a thickness of the platform, created by a distance between the first platform surface and the second platform surface, is smaller at the edge of the platform than in a center of the platform.

2. The top piece according to claim 1, wherein the platform and the connecting pin are formed as one piece.

3. The top piece according to claim 1, wherein the top piece is made out of titanium.

4. The top piece according to claim 3, wherein the platform, in a view from above onto the second platform surface, extends over a total angular area of 360° and has a diameter, and wherein the diameter of the platform is large enough that, at least over a part of the total angular area, in a state in which the top piece is connected with the corresponding pin-shaped dental implant, in the view from above onto the second platform surface, the platform protrudes over the corresponding pin-shaped dental implant.

5. The top piece according to claim 3, wherein, in a state in which the top piece is connected to a corresponding pin-shaped dental implant, in a view from above onto the second platform surface, the platform protrudes over the corresponding pin-shaped dental implant over a total angular area.

6. The top piece according to claim 3, wherein, in a view from above onto the second platform surface, a diameter of the platform is nowhere smaller than a diameter of the pin-shaped dental implant at an implant shoulder over a total angular area.

7. The top piece according to claim 1, wherein, at least the platform, and the retention pin are formed as one piece.

8. The top piece according to claim 7, wherein, at least the platform, the retention pin, and the connecting pin are formed as one piece.

9. The top piece according to claim 1, further comprising a processing sleeve on the connecting pin for protection during processing of the platform.

10. An arrangement comprising:
    a pin-shaped dental implant having a blind bore, and
    a top piece according to claim 1, the connecting pin of the top piece being inserted in the blind bore.

11. The arrangement according to claim 10, wherein a mesostructure is mounted onto the top piece.

12. A method for anatomic adaptation of the top piece according to claim 1, comprising reducing in size a diameter of the platform at least over a part of a total angular area outside a body of a patient by removing material such that the platform is adapted to dimensions of the mesostructure to be fastened to the platform, oriented at adjoining teeth of the patient.

13. The top piece according to claim 1, wherein the connecting pin has a pin diameter in a vicinity of an end of the second platform surface, and wherein a diameter of the platform is, at least over a part of a total angular area, larger than the pin diameter.

14. The top piece according to claim 13, wherein a ratio of the diameter of the platform to the pin diameter is smaller than 18.

15. The top piece according to claim 13, wherein a ratio of the diameter of the platform to the pin diameter is larger than 2.

16. The top piece according to claim 15, wherein the ratio of the diameter of the platform to the pin diameter is larger than 3.

17. The top piece according to claim 1, wherein the platform, in a view from above onto the second platform surface, extends over a total angular area of 360° and has a diameter, and wherein the diameter of the platform is large enough that, at least over a part of the total angular area, in a state in which the top piece is connected with a corresponding pin-shaped dental implant, in the view from above onto the second platform surface, the platform protrudes over the corresponding pin-shaped dental implant.

18. The top piece according to claim 1, wherein:
    the edge of the platform is a first edge at a first side of the platform, and
    the platform has a second edge at a second side of the platform, the second edge being arched in the coronal direction, away from the connecting pin.

19. The top piece according to claim 1, wherein a space is defined between the retention pin and the platform.

20. The top piece according to claim 1, wherein the thickness of the center of the platform is 0.8 millimeters.

21. The top piece according to claim 1, wherein each of an edge of the first platform surface and an edge of the second platform surface is arcuately arched so as to define the edge of the platform which is arched.

22. The top piece according to claim 1, wherein the retention pin includes an anti-rotation lock.

23. An arrangement comprising:
    a mesostructure,
    a pin-shaped dental implant, and a top piece comprising a platform having a first platform surface and a second platform surface, a retention pin mounted on the first platform surface for fastening of the mesostructure, and a connecting pin for connecting the platform with a blind bore of the pin-shaped dental implant corresponding to the connecting pin,
wherein:
an edge of the platform is arched in a coronal direction, away from the connecting pin, which results in a plate-shaped formation of the first platform surface such that a central portion of the first platform surface is flat,
a proximal end of the mesostructure is between a first edge of the first platform surface and a second edge of the first platform surface such that the mesostructure occupies a space between the retention pin and the platform, and
each of the first edge of the first platform surface and a first edge of the second platform surface is arcuately arched so as to define the edge of the platform which is arched.

24. The arrangement according to claim 23, wherein the mesostructure is in contact with the platform between the first edge of the first platform surface and the second edge of the first platform surface.

25. The arrangement according to claim 24, wherein an entirety of a bottom surface of the mesostructure is in contact with the platform between the first edge of the first platform surface and the second edge of the first platform surface.

26. The arrangement according to claim 23, wherein the retention pin includes an anti-rotation lock.

27. A top piece for a corresponding pin-shaped dental implant, the top piece comprising:
a platform having a first platform surface and a second platform surface,
a retention pin mounted on the first platform surface for fastening of a mesostructure, and
a connecting pin for connecting the platform with a blind bore of a pin-shaped dental implant corresponding to the connecting pin,
wherein:
an edge of the platform is arched in a coronal direction, away from the connecting pin, which results in a plate-shaped formation of the first platform surface such that a central portion of the first platform surface is flat, and
at least the platform, and the retention pin are formed as one piece.

28. The top piece according to claim 27, wherein the platform and the connecting pin are formed as one piece.

29. The top piece according to claim 27, wherein the top piece is made out of titanium.

30. The top piece according to claim 29, wherein the platform, in a view from above onto the second platform surface, extends over a total angular area of 360° and has a diameter, and wherein the diameter of the platform is large enough that, at least over a part of the total angular area, in a state in which the top piece is connected with the corresponding pin-shaped dental implant, in the view from above onto the second platform surface, the platform protrudes over the corresponding pin-shaped dental implant.

31. The top piece according to claim 29, wherein, in a state in which the top piece is connected to a corresponding pin-shaped dental implant, in a view from above onto the second platform surface, the platform protrudes over the corresponding pin-shaped dental implant over a total angular area.

32. The top piece according to claim 29, wherein, in a view from above onto the second platform surface, a diameter of the platform is nowhere smaller than a diameter of the pin-shaped dental implant at an implant shoulder over a total angular area.

33. The top piece according to claim 27, further comprising a processing sleeve on the connecting pin for protection during processing of the platform.

34. An arrangement comprising:
a pin-shaped dental implant having a blind bore, and
a top piece according to claim 27, the connecting pin of the top piece being inserted in the blind bore.

35. The arrangement according to claim 34, wherein a mesostructure is mounted onto the top piece.

36. A method for anatomic adaptation of the top piece according to claim 27, comprising reducing in size a diameter of the platform at least over a part of a total angular area outside a body of a patient by removing material such that the platform is adapted to dimensions of the mesostructure to be fastened to the platform, oriented at adjoining teeth of the patient.

37. The top piece according to claim 27, wherein the connecting pin has a pin diameter in a vicinity of an end of the second platform surface, and wherein a diameter of the platform is, at least over a part of a total angular area, larger than the pin diameter.

38. The top piece according to claim 37, wherein a ratio of the diameter of the platform to the pin diameter is smaller than 18.

39. The top piece according to claim 37, wherein a ratio of the diameter of the platform to the pin diameter is larger than 2.

40. The top piece according to claim 39, wherein the ratio of the diameter of the platform to the pin diameter is larger than 3.

41. The top piece according to claim 27, wherein, at least the platform, the retention pin, and the connecting pin are formed as one piece.

42. The top piece according to claim 27, wherein the platform, in a view from above onto the second platform surface, extends over a total angular area of 360° and has a diameter, and wherein the diameter of the platform is large enough that, at least over a part of the total angular area, in a state in which the top piece is connected with a corresponding pin-shaped dental implant, in the view from above onto the second platform surface, the platform protrudes over the corresponding pin-shaped dental implant.

43. The top piece according to claim 27, wherein:
the edge of the platform is a first edge at a first side of the platform, and
the platform has a second edge at a second side of the platform, the second edge being arched in the coronal direction, away from the connecting pin.

44. The top piece according to claim 27, wherein a space is defined between the retention pin and the platform.

45. The top piece according to claim 27, wherein a thickness of a center of the platform is 0.8 millimeters.

46. The top piece according to claim 27, wherein each of an edge of the first platform surface and an edge of the second platform surface is arcuately arched so as to define the edge of the platform which is arched.

47. The top piece according to claim 27, wherein the retention pin includes an anti-rotation lock.

48. A top piece for a corresponding pin-shaped dental implant, the top piece comprising:
- a platform having a first platform surface and a second platform surface,
- a retention pin mounted on the first platform surface for fastening of a mesostructure, and
- a connecting pin for connecting the platform with a blind bore of a pin-shaped dental implant corresponding to the connecting pin,
- wherein:
  - an edge of the platform is arched in a coronal direction, away from the connecting pin, which results in a plate-shaped formation of the first platform surface such that a central portion of the first platform surface is flat, and
  - each of an edge of the first platform surface and an edge of the second platform surface is arcuately arched so as to define the edge of the platform which is arched.

49. The top piece according to claim 48, wherein the platform and the connecting pin are formed as one piece.

50. The top piece according to claim 48, wherein the top piece is made out of titanium.

51. The top piece according to claim 50, wherein the platform, in a view from above onto the second platform surface, extends over a total angular area of 360° and has a diameter, and wherein the diameter of the platform is large enough that, at least over a part of the total angular area, in a state in which the top piece is connected with the corresponding pin-shaped dental implant, in the view from above onto the second platform surface, the platform protrudes over the corresponding pin-shaped dental implant.

52. The top piece according to claim 50, wherein, in a state in which the top piece is connected to a corresponding pin-shaped dental implant, in a view from above onto the second platform surface, the platform protrudes over the corresponding pin-shaped dental implant over a total angular area.

53. The top piece according to claim 50, wherein, in a view from above onto the second platform surface, a diameter of the platform is nowhere smaller than a diameter of the pin-shaped dental implant at an implant shoulder over a total angular area.

54. The top piece according to claim 48, further comprising a processing sleeve on the connecting pin for protection during processing of the platform.

55. An arrangement comprising:
- a pin-shaped dental implant having a blind bore, and
- a top piece according to claim 48, the connecting pin of the top piece being inserted in the blind bore.

56. The arrangement according to claim 55, wherein a mesostructure is mounted onto the top piece.

57. A method for anatomic adaptation of the top piece according to claim 48, comprising reducing in size a diameter of the platform at least over a part of a total angular area outside a body of a patient by removing material such that the platform is adapted to dimensions of the mesostructure to be fastened to the platform, oriented at adjoining teeth of the patient.

58. The top piece according to claim 48, wherein the connecting pin has a pin diameter in a vicinity of an end of the second platform surface, and wherein a diameter of the platform is, at least over a part of a total angular area, larger than the pin diameter.

59. The top piece according to claim 58, wherein a ratio of the diameter of the platform to the pin diameter is smaller than 18.

60. The top piece according to claim 58, wherein a ratio of the diameter of the platform to the pin diameter is larger than 2.

61. The top piece according to claim 60, wherein the ratio of the diameter of the platform to the pin diameter is larger than 3.

62. The top piece according to claim 48, wherein, at least the platform, the retention pin, and the connecting pin are formed as one piece.

63. The top piece according to claim 48, wherein the platform, in a view from above onto the second platform surface, extends over a total angular area of 360° and has a diameter, and wherein the diameter of the platform is large enough that, at least over a part of the total angular area, in a state in which the top piece is connected with a corresponding pin-shaped dental implant, in the view from above onto the second platform surface, the platform protrudes over the corresponding pin-shaped dental implant.

64. The top piece according to claim 48, wherein:
- the edge of the platform is a first edge at a first side of the platform, and
- the platform has a second edge at a second side of the platform, the second edge being arched in the coronal direction, away from the connecting pin.

65. The top piece according to claim 48, wherein a space is defined between the retention pin and the platform.

66. The top piece according to claim 48, wherein a thickness of a center of the platform is 0.8 millimeters.

67. The top piece according to claim 48, wherein the retention pin includes an anti-rotation lock.

\* \* \* \* \*